United States Patent
Liu et al.

(10) Patent No.: US 12,297,114 B2
(45) Date of Patent: May 13, 2025

(54) TERAHERTZ MATERIAL WITH THERAPEUTIC AND HEALTH CARE EFFECT AND ITS PREPARATION METHOD AND APPLICATION

(71) Applicant: Henan Jingpin New Material Technology Co., Ltd., Zhengzhou (CN)

(72) Inventors: Quanxue Liu, Tianjin (CN); Yunfeng Nie, Tianjin (CN); Hengzhuo Liu, Tianjin (CN); Yan Tong, Tianjin (CN); Wenhao Hou, Tianjin (CN)

( * ) Notice: Subject to any disclaimer, the term of this patent is extended or adjusted under 35 U.S.C. 154(b) by 629 days.

(21) Appl. No.: 17/621,074

(22) PCT Filed: Jun. 18, 2020

(86) PCT No.: PCT/CN2020/096830
§ 371 (c)(1),
(2) Date: Dec. 20, 2021

(87) PCT Pub. No.: WO2020/253782
PCT Pub. Date: Dec. 24, 2020

(65) Prior Publication Data
US 2022/0348473 A1   Nov. 3, 2022

(30) Foreign Application Priority Data
Jun. 18, 2019 (CN) .......................... 201910527301.2

(51) Int. Cl.
*C01B 33/12* (2006.01)
*A61K 9/20* (2006.01)
(Continued)

(52) U.S. Cl.
CPC ................ *C01B 33/12* (2013.01); *A61K 9/20* (2013.01); *A61K 33/00* (2013.01); *A61N 5/06* (2013.01); *A61N 2005/0659* (2013.01)

(58) Field of Classification Search
CPC .......... C01B 33/12; A61K 9/20; A61K 33/00; A61N 5/06; A61N 2005/0659;
(Continued)

(56) References Cited

FOREIGN PATENT DOCUMENTS

CN            1085588 A    *   4/1994

* cited by examiner

*Primary Examiner* — Richard M Rump
(74) *Attorney, Agent, or Firm* — Novoclaims Patent Services LLC; Mei Lin Wong

(57) ABSTRACT

The present invention discloses a terahertz material with therapeutic and health care effect and its preparation method and application, which includes the following raw materials in parts by weight: 15~28 $SiO_2$, 3~8 $Al_2O_3$, 1~3 selenium, 2~5 germanium, 10~15 $Fe_2O_3$, 35~45 ochre, 20~35 zinc oxide, 65~80 $CaCO_3$, 0.1~0.5 rare earth palladium, 1~10 $SiO_x$, wherein the raw materials of components are mixed according to the above proportion, and crushing, heating to 600~1200° C. in an oxygen free environment for 3~8 hours, and then secondary crushing, having a fineness of 3000~8000 mesh; and then, after crushing again and powdering processing, the fineness reaches more than 10000 mesh. After being enhanced treatment by the terahertz irradiation line, the terahertz materials with therapeutic and health care effects are obtained. They can be processed and manufactured into a variety of physiotherapy equipment, with fast action speed and stable effect on human body.

3 Claims, 8 Drawing Sheets

40-terahertz physiotherapy tablet, 50-heater,
360-physiological underwear

(51) Int. Cl.
*A61K 33/00* (2006.01)
*A61N 5/06* (2006.01)

(58) Field of Classification Search
CPC ........... C09C 1/0009; C09C 1/12; C09C 1/24; C09C 1/28
See application file for complete search history.

1-human, 2-terahertz irradiation range, 3-lesion site,
4- physiotherapy tablet 1-human, 2-terahertz irradiation range, 3-lesion site,
4- physiotherapy tablet (containing the terahertz material of the present invention), 5-heater 6-combined physiotherapy tablet (4-physiotherapy tablet and 5-heater), 7-cable, 8-timer, 9-temperature setting, 10-physiotherapy instrument host 6-combined physiotherapy tablet (4-physiotherapy tablet and 5-heater), 7-cable, 8-timer, 9-temperature setting, 10-physiotherapy instrument host, 11-sleeping bag 6-combined physiotherapy tablet (4-physiotherapy tablet and 5-heater), 7-cable,
8-timer, 9-temperature setting, 10-physiotherapy instrument host,
12-semicircular cover, 13-bed board and mattress, 14-pillow 6-combined physiotherapy tablet (4-physiotherapy tablet and 5-heater),
7-cable, 10-physiotherapy instrument host, 15-upper cover,
16- physiotherapy instrument body

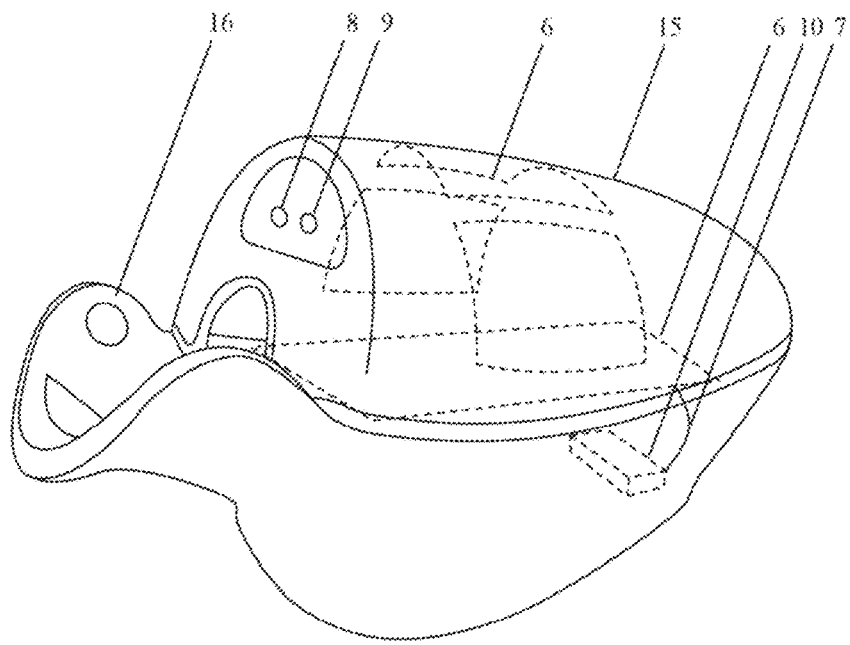

FIG.7

6-combined physiotherapy tablet (4-physiotherapy tablet and 5-heater), 7-cable, 8-timer, 9-temperature setting, 10-physiotherapy instrument host, 15-upper cover, 16-physiotherapy instrument body

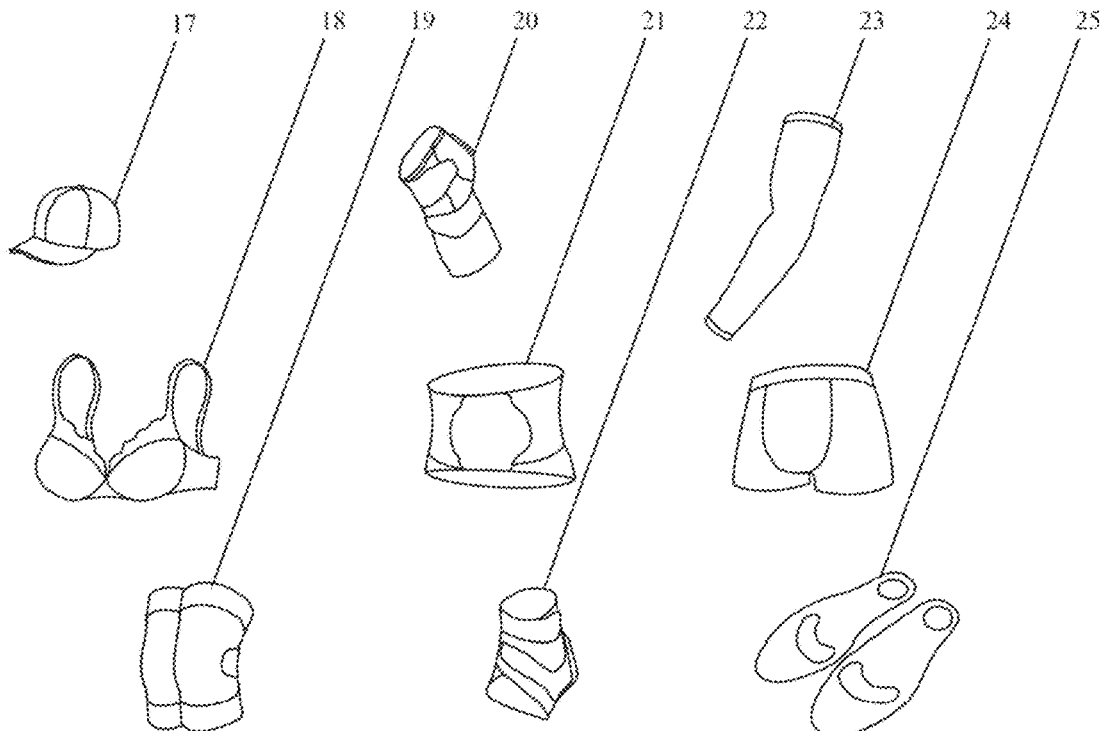

FIG.8

17-physiotherapy wristband, 18-physiotherapy elbow, 19-physiotherapy waist, 20-physiotherapy underwear, 21- physiotherapy knee, 22-physiotherapy ankle, 23-physiotherapy insole, 24-physiotherapy mattress, 25-hysiotherapy pillow 26-physiotherapy mattress, 27-physiotherapy pillow, 28-physiotherapy waist, 29-physiotherapy underwear, 30-physiotherapy quilt

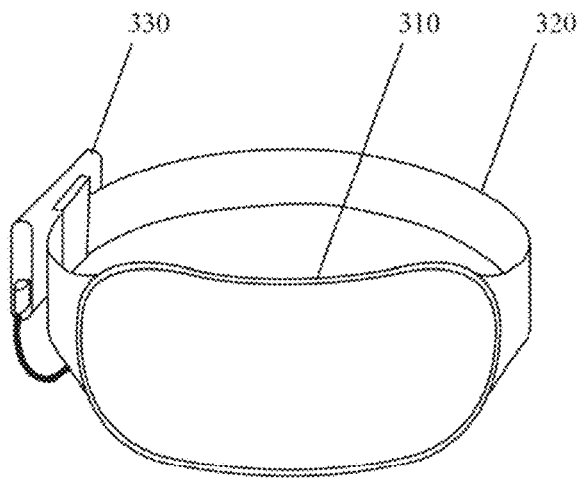
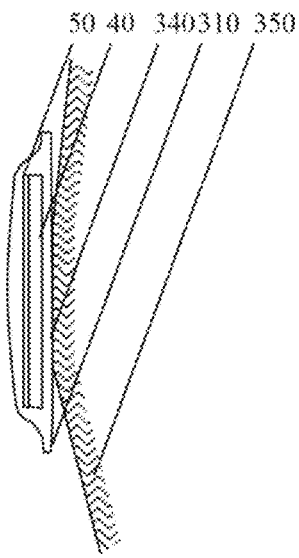
FIG.14                FIG.15
40-terahertz physiotherapy tablet, 50-heater, 310-physiotherapy belt (40-the terahertz physiotherapy tablet and 50-the heater are placed inside), 320-elastic band, 330-controller and power supply, 340-comfort layer, 350-belly
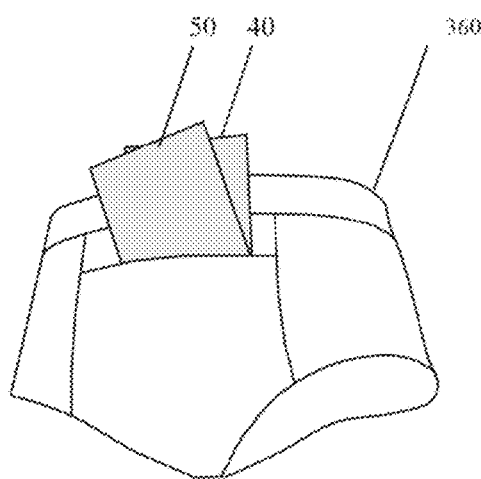
FIG.16
40-terahertz physiotherapy tablet, 50-heater, 360-physiological underwear

TERAHERTZ MATERIAL WITH THERAPEUTIC AND HEALTH CARE EFFECT AND ITS PREPARATION METHOD AND APPLICATION

CROSS REFERENCE OF RELATED APPLICATION

This application claims the benefit under 35 U.S.C. § 119 from International Application No. PCT/CN 2020/096830, which claims priorities to CN 201910527301.2, filed Jun. 18, 2019.

BACKGROUND OF THE PRESENT INVENTION

Field of Invention

The present invention relates to the technical field of terahertz, and more particularly to a terahertz material with therapeutic and health care effect and its preparation method and application.

Description of Related Arts

At present, an infrared physiotherapy has been very popular. However, the therapeutic effect is not very ideal and can only be used as an adjuvant therapy and rehabilitation means. At the same time, the equipment is large in size and the completely portable products only are the products such as a warm baby and a self-heating sticker. The waste used by these products pollutes the environment. Domestic double-sided adhesive tapes generally cause allergies and are not convenient for continuous use for many days. Even if they are used continuously, they have almost no therapeutic effect.

SUMMARY OF THE PRESENT INVENTION

The present invention discloses a terahertz material with therapeutic and health care effect and its preparation method and application, aiming at the problems existing in the prior art.

In order to solve the above technical problems, the invention adopts the following technical solutions:

A terahertz material with therapeutic and health care effect, which includes the following raw materials in parts by weight: 15~28 $SiO_2$, 3~8 $Al_2O_3$, 1~3 selenium, 2~5 germanium, 10~15 $Fe_2O_3$, 35~45 ochre, 20~35 zinc oxide, 65~80 $CaCO_3$, 0.1~0.5 rare earth palladium, 1~10 $SiO_x$.

The preparation method the of terahertz material with therapeutic and health care effect, comprising the following steps:

(1) mixing crude silicon, $SiO_2$ and Binchotan in a weight ratio of 1:(3~5):(5~10), and heating to 700~1500° C. in an oxygen-free environment for 1~8 hours to obtain a black crystal $SiO_x$;

(2) mixing the prepared $SiO_x$ with other raw materials in accordance with the stated proportions, crushing, its fineness reaches 200~500 mesh, and adding an appropriate amount of water, stirring (It is better to form balls), being turn into small balls through a circular rotary table, heating to 600~1200° C. in an oxygen free environment for 3~8 hours, and carrying out a secondary crushing, its fineness reaches 3000~8000 mesh;

(3) detecting its infrared emissivity, which is ≥0.92, and then crushing and powdering process, its fineness reaches is more than 10000 mesh, after being enhanced by a plurality of terahertz irradiation line to obtain a terahertz material with therapeutic and health care effect.

The terahertz irradiation line for enhancing process is configured to have 1-7 different frequencies, which are $2.3\times10^{11}$, $5.5\times10^{11}$, $1.1\times10^{12}$, $2.3\times10^{12}$, $5.5\times10^{12}$, $1.1\times10^{13}$ and $2.3\times10^{13}$ Hz respectively.

the terahertz irradiation light source includes a terahertz irradiation assembly, a transmission belt and a tunnel frame, the terahertz irradiation assembly is installed on the tunnel frame, the transmission belt is arranged through the tunnel frame, and the terahertz irradiation assembly is matched with the transmission belt, wherein the terahertz irradiation assembly comprises a terahertz wave electron generator and a cable, wherein the terahertz wave electron generator comprises a logic unit, a fundamental wave unit, an equalization circuit, an amplifier and a radiator, wherein the terahertz wave electron generator is connected with the radiator through a cable, and the radiator is attached on the inner wall of the tunnel frame.

The fundamental wave unit comprises a plurality of fundamental wave modules arranged in parallel, and the fundamental wave module comprises a driver, a BAW filter, a charge pump, an electro-photon transition module and a resonant cavity, wherein the logic unit controls the opening and closing of the charge pump through the driver, an external power supply supplies power to the electric photon transition module through the BAW filter and the charge pump, and the electron beam generated in the electric photon transition module is transmitted to the resonant cavity to generate a stable terahertz fundamental wave, wherein the logic unit controls each fundamental wave module to transmit terahertz fundamental wave, which is transmitted to the equalization circuit, wherein the equalization circuit modulates the received terahertz fundamental wave to obtain a composite terahertz wave, wherein the composite terahertz wave is transmitted to the amplifier, and the amplifier amplifies the received composite terahertz wave to obtain an amplified terahertz wave, wherein the amplified terahertz wave is transmitted to the radiator.

The electro-photon transition module comprises an electron gun, a pulse deflection coil, an electron beam, an anode and a transition cavity, wherein the transition cavity is communicated with the resonant cavity, the electron gun and the pulse deflection coil are installed within the transition cavity, and a frequency selective electric field is formed between the pulse deflection coil, wherein the anode is installed on the inner wall of the resonant cavity the electron gun is communicated with the external power supply through the charge pump and the BAW filter, wherein the electron gun emits an electron beam into the frequency selected electric field constructed by the pulse deflection coil 036, wherein the frequency selected electron beam enters the resonant cavity and is received by anode to generate the terahertz fundamental wave.

An application of the terahertz material with therapeutic and health care effect in dysmenorrhea relieving/treating products: adding the terahertz material into a silica gel substrate to make a silica gel physiotherapy tablet and placing the silica gel physiotherapy tablet in a physiological underwear; or making the terahertz material into a silica gel physiotherapy tablet and placing the silica gel physiotherapy tablet in a physiotherapy bag, wherein the addition amount of the terahertz material in the silica gel physiotherapy tablet is 10~55 wt %, wherein the preparation method of the silica gel physiotherapy tablet is the same as that of the conventional silicon tablet; or, using the terahertz material with therapeutic and health care effect in the form of hot compress bags; or adding it to existing products such as "warm baby" for application.

An application of the terahertz material with therapeutic and health care effect in preparing a physiotherapy equipment: using the terahertz material as one of the raw materials of the physiotherapy equipment to prepare the physiotherapy equipment, or adding the terahertz material into a silica gel substrate to make a silica gel physiotherapy tablet, which is applied in various physiotherapy equipment, wherein the physiotherapy equipment includes but is not limited to a physiotherapy instrument, a physiotherapy sleeping bag, a tunnel physiotherapy warehouse, a sitting physiotherapy warehouse, a lying down physiotherapy warehouse, wherein the addition amount of the terahertz material in the silica gel physiotherapy tablet is 10~55 wt %, wherein the preparation method of the silica gel physiotherapy tablet is the same as that of the conventional silicon tablet.

Terahertz frequency is defined by many experts at the far end of the far infrared. This frequency is just similar to the rotation frequency of electrons in atoms. Therefore, terahertz wave can resonate with the atoms that make up cells (especially the polar molecule water), improve molecular activity and permeability, and then open blood vessels. Because terahertz wave has the fingerprint characteristics of the structure and properties of reactive substances, and the photon energy is low, which is far less than the energy of X-rays, it will not produce harmful ionization to biological macromolecules, biological cells and tissues (excerpted from research on biomedical application of terahertz technology in China, science and Technology Daily, Apr. 13, 2014). Therefore, the treatment process is very safe.

The terahertz material of the present invention can be processed and manufactured into a variety of physiotherapy equipment, which can be heated or used at room temperature. It can be physiotherapy equipment, protective equipment, bedding, etc. These physiotherapy equipment can treat all kinds of bone and flesh pain, dizziness, insomnia, inflammation, immune diseases, advanced cancer and other common diseases.

The terahertz material powder with therapeutic and health care effect, provided by the present invention, can be manufactured into a device with physiotherapy, health care and therapeutic effects. After many tests, it is proved that the material has fast action speed, stable effect and no side effects on human body, and these devices can be reused.

Beneficial effects of the present invention: compared with the prior art, the terahertz material for health treatment of the present invention has the following beneficial effects: 1) accelerating metabolism, especially accelerating urination, which can have an obvious feeling when used for the first time. Most people's urination time is shortened to ½~¼ of the original; 2) Detoxify quickly and reflect it on the skin. After a week of use, the skin will become smoother and freckles will obviously fade; 3) Opening up the meridians can detoxify, prevent cardiovascular and cerebrovascular diseases, keep the skin moist and improve memory. At present, although it is uncertain that the terahertz physiotherapy is better than acupuncture, cupping, massage and acupoint lighting, the terahertz physiotherapy has an incomparable advantage, that is, it can carry out treatment and physiotherapy without professional skills, and it goes directly to the meridians of the whole body; 4) It has the fastest effect on a qi stagnation, dampness and cold body constitution. It has special effects on sleep disorders, body cold, endless dripping and dysmenorrhea, and quickly improves the water environment in the body; 5) rapidly enhance immunity. Cooperating with terahertz drinking water, can treat many kinds of immune system diseases. there are some successful cured malignant tumor and terminal cancer cases, and more vitiligo and AIDS treatment tests are still in progress; 6) Local rapid analgesia, it can quickly relieve various muscle and nerve pain, and cure sciatica, lumbar disc herniation, tenosynovitis, heel tendinitis and tennis elbow.

BRIEF DESCRIPTION OF THE DRAWINGS

FIG. 7 shows a high temperature application of a lying down physiotherapy warehouse made of the above terahertz material with health treatment effect of the present invention.

FIG. 8 shows a physiotherapy clothing made of the above terahertz material with health treatment effect of the present invention.

FIG. 14 shows a dysmenorrhea treatment belt with a terahertz physiotherapy tablet having a heating equipment of the present invention.

FIG. 15 is a use state diagram of the above dysmenorrhea treatment belt with a terahertz physiotherapy tablet having a heating equipment of the present invention.

FIG. 16 shows a treatment of dysmenorrhea provided by combining a physiological underwear and a warm baby with the above terahertz physiotherapy tablet.

Figure 1:
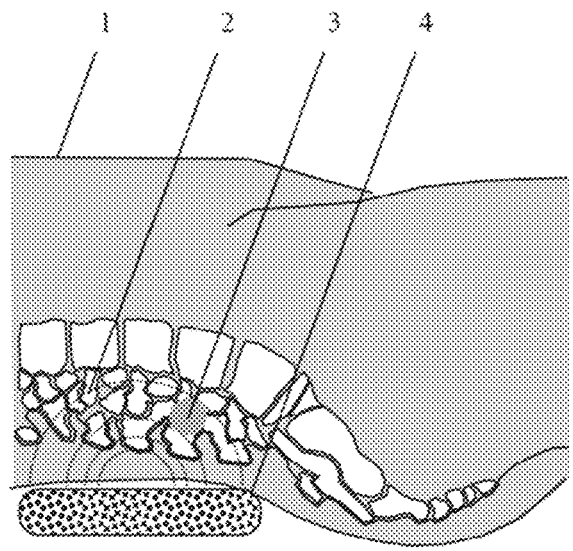
FIG. 1 shows a normal temperature application of a physiotherapy tablet made of a terahertz material with health treatment effect of the present invention.

Description of the reference numbers: the reference number 1 represents a human being, the reference number 2 represents a terahertz irradiation range, the reference number 3 represents a lesion site, the reference number 4 represents a physiotherapy tablet (containing the terahertz material of the present invention), the reference number 5 represents a heater, the reference number 6 represents a combined physiotherapy tablet (including 4—the physiotherapy tablet and 5—the heater), the reference number 7 represents a cable, the reference number 8 represents a timer, the reference number 9 represents a temperature setting, the reference number 10 represents a physiotherapy instrument host, the reference number 11 represents a sleeping bag, the reference number 12 represents a semicircular cover, the reference number 13 represents a bed board and mattress, the reference number 14 represents a pillow, the reference number 15 represents an upper cover, the reference number 16 represents a physiotherapy instrument body, the reference number 17 represents a physiotherapy wristband, the reference number 18 represents a physiotherapy elbow, the reference number 19 represents a physiotherapy waist, the reference number 20 represents a physiotherapy underwear, the reference number 21 represents a physiotherapy knee, the reference number 22 represents a physiotherapy ankle, the reference number 23 represents a physiotherapy insole, the reference number 24 represents a physiotherapy mattress, the reference number 25 represents a physiotherapy pillow, the reference number 19 represents a physiotherapy mattress, the reference number 20 represents a physiotherapy quilt, the reference number 017 represents a terahertz wave electronic generator, the reference number 018 represents a roasted terahertz material semi-finished products, the reference number 015 represents a cable, the reference number 012 represents a tunnel frame, the reference number 011 represents a transmission belt, the reference number 01 represents a logic unit, the reference number 02 represents a fundamental unit, the reference number 03 represents an equalizing circuit, the reference number 04 represents an amplifier, the reference number 05 represents a radiator, the reference number 06 represents a driver, the reference number 07 represents a BAW filter, the reference number 08 represents a charge pump, the reference number 09 represents an electro-photon transition module, the reference number 010 represents an electron beam transmitted to the resonant cavity, the reference number 035 represents an electron gun, the reference number 036 represents a pulse deflection coil, the reference number 037 represents an electron beam, the reference number 038 represents an anode, the reference number 039 represents a transition cavity, the reference number 40 represents a terahertz physiotherapy tablet, the reference number 50 represents a heater, the reference number 310 represents a physiotherapy belt (40—the terahertz physiotherapy tablet and 50—the heater are placed inside), the reference number 320 represents an elastic band, the reference number 330 represents a controller and a power supply, the reference number 340 represents a comfort layer, the reference number 350 represents a belly and the reference number 360 represents a physiological underwear.

DETAILED DESCRIPTION OF THE PREFERRED EMBODIMENT

In order to make the object, technical scheme and advantages of the present invention clearer, the present invention is further described below in combination with embodiments:

Example 1

A terahertz material with therapeutic and health care effect, which includes the following raw materials in parts by weight: 20 $SiO_2$, 4 $Al_2O$, 2 selenium, 3 germanium, 12 $Fe_2O_3$, 40 ochre, 25 zinc oxide, 70 $CaCO_3$, 0.3 rare earth palladium, 5 $SiO_x$.

The preparation method of the terahertz material with therapeutic and health care effect, comprising the following steps:

(1) mixing crude silicon, $SiO_2$ and Binchotan in a weight ratio of 1:4:8, and heating to 1200° C. in an oxygen-free environment for 3 hours to obtain a black crystal $SiO_x$;

(2) mixing the prepared $SiO_x$ with other raw materials in accordance with the stated proportions, crushing, its fineness reaches 200~500 mesh, and adding an appropriate amount of water, stirring, being turn into a small ball through a circular rotary table, heating to 1000° C. in an oxygen free environment for 4 hours, and carrying out a secondary crushing, its fineness reaches 3000~8000 mesh;

(3) detecting its infrared emissivity, which is ≥0.92, and then crushing and powdering process, its fineness reaches is more than 10000 mesh, after being enhanced by a plurality of terahertz irradiation line to obtain a terahertz material with therapeutic and health care effect, wherein the terahertz irradiation line for enhancing process are configured to have 1-7 different frequencies, which are $2.3\times10^{11}$, $5.5\times10^{11}$, $1.1\times10^{12}$, $2.3\times10^{12}$, $5.5\times10^{12}$, $1.1\times10^{13}$, $2.3\times10^{13}$ Hz respectively.

Figure 10:
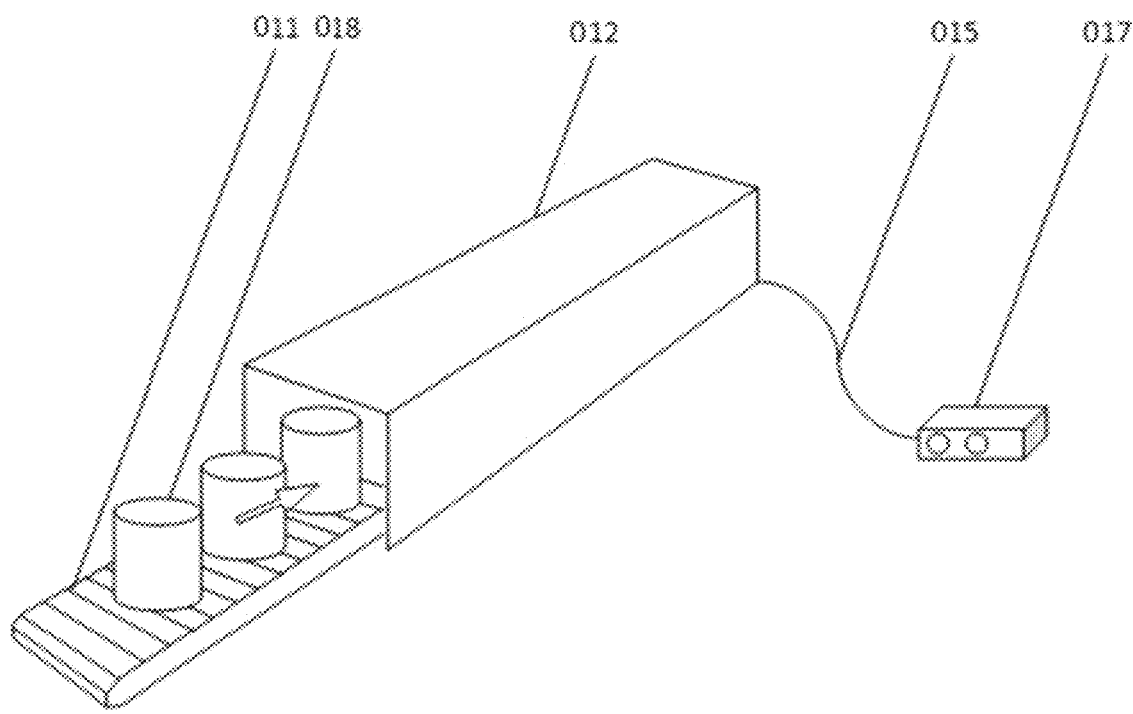
FIG. 10 shows a structure diagram of the terahertz irradiation light source of the present invention.

As shown in FIG. 10, the terahertz irradiation light source comprises a terahertz irradiation assembly, a transmission belt 011 and a tunnel frame 012, wherein the terahertz irradiation assembly is installed on the tunnel frame 012, the transmission belt 011 is arranged through the tunnel frame 012, and the terahertz irradiation assembly is matched with the transmission belt 011, wherein the terahertz irradiation assembly comprises a terahertz wave electron generator and a cable, wherein the terahertz wave electron generator comprises a logic unit 01, a fundamental wave unit 02, an equalization circuit 03, an amplifier 04 and a radiator 05, wherein the terahertz wave electron generator is connected with the radiator 05 through a cable, and the radiator 05 is attached on the inner wall of the tunnel frame 012.

Figure 11:
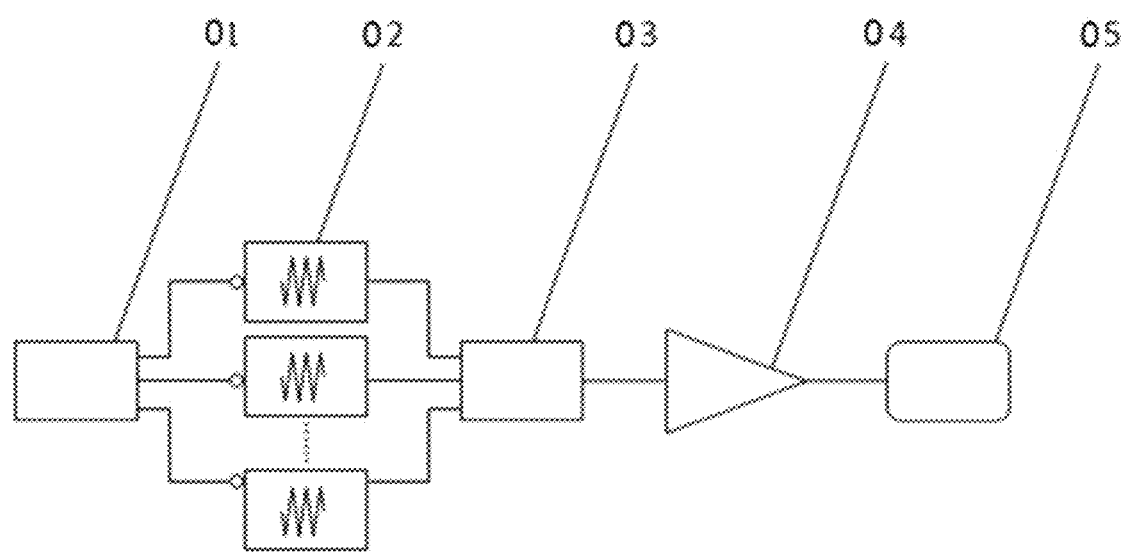
FIG. 11 is a schematic diagram of the terahertz wave electron generator shown in FIG. 7.
Figure 12:
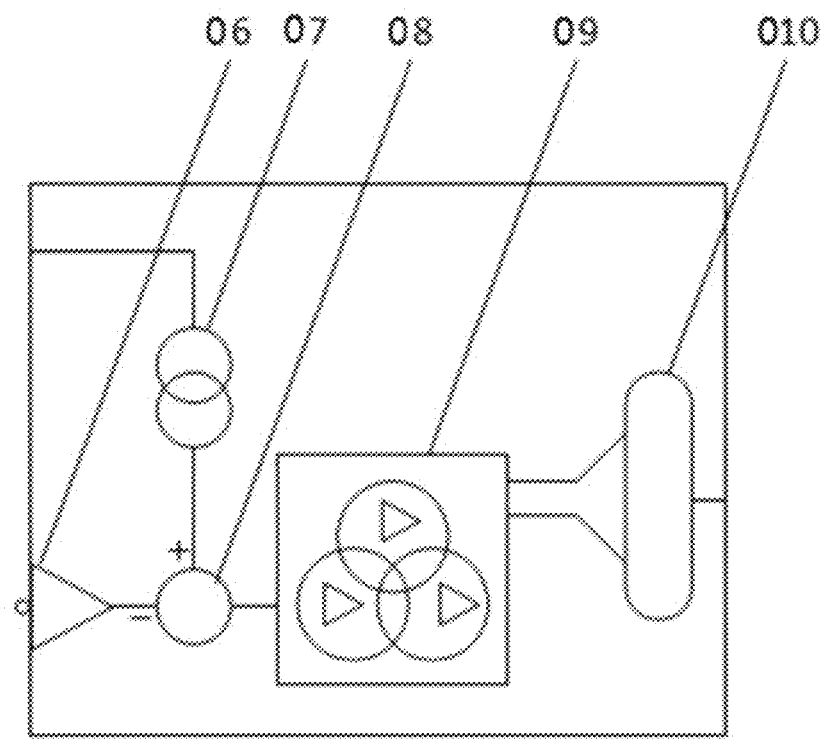
FIG. 12 is a schematic diagram of the fundamental wave module shown in FIG. 8.

As shown in FIGS. 11 and 12, the fundamental wave unit 02 comprises a plurality of fundamental wave modules arranged in parallel, and the fundamental wave module comprises a driver 06, a BAW filter 07, a charge pump 08, an electro-photon transition module 09 and a resonant cavity 010, wherein the logic unit 01 controls the opening and closing of the charge pump 08 through the driver 06, an external power supply supplies power to the electric photon transition module 09 through the BAW filter 07 and the charge pump 08, and the electron beam generated in the electric-photon transition module 09 is transmitted to the resonant cavity 010 to generate a stable terahertz fundamental wave, wherein the logic unit 01 controls each fundamental wave module to transmit terahertz fundamental wave, which is transmitted to the equalization circuit 03, wherein the equalization circuit 03 modulates the received terahertz fundamental wave to obtain a composite terahertz wave, wherein the composite terahertz wave is transmitted to the amplifier 04, and the amplifier 04 amplifies the received composite terahertz wave to obtain an amplified terahertz wave, wherein the amplified terahertz wave is transmitted to the radiator 05.

Figure 13:
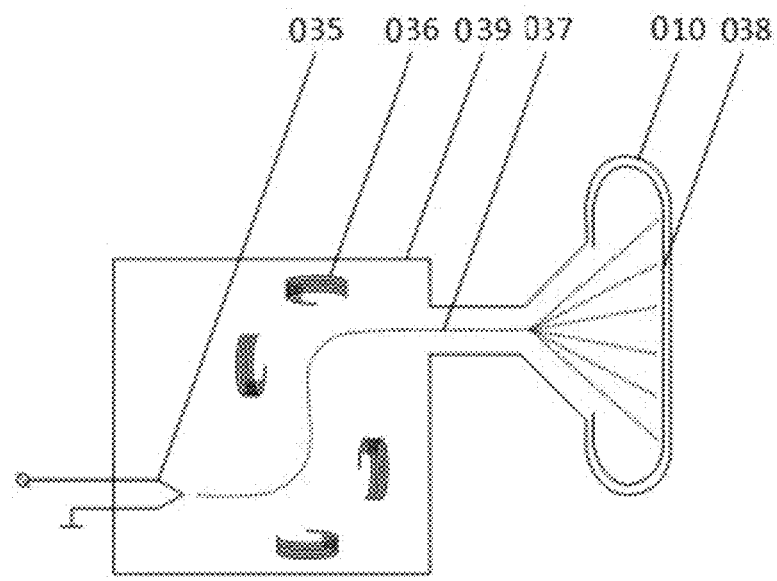
FIG. 13 is a schematic diagram of the electro photonic transition module shown in FIG. 9.

As shown in FIG. 13, the electro-photon transition module 09 comprises an electron gun 035, a pulse deflection coil 036, an electron beam 037, an anode 038 and a transition cavity 039, wherein the transition cavity 039 is communicated with the resonant cavity 010, the electron gun 035 and the pulse deflection coil 036 are installed within the transition cavity 039, and a frequency selective electric field is formed between the pulse deflection coil 036, wherein the anode 038 is installed on the inner wall of the resonant cavity 010, the electron gun 035 is communicated with the external power supply through the charge pump 08 and the BAW filter 07, wherein the electron gun 035 emits an electron beam into the frequency selected electric field constructed by the pulse deflection coil 036, wherein the frequency selected electron beam enters the resonant cavity 010 and is received by the anode 038 to generate the terahertz fundamental wave.

Example 2

A terahertz material with therapeutic and health care effect, which includes the following raw materials in parts by weight: 15 $SiO_2$, 8 $Al_2O_3$, 1 selenium, 5 germanium, 10 $Fe_2O_3$, 45 ochre, 20 zinc oxide, 80 $CaCO_3$, 0.1 rare earth palladium, 10 $SiO_x$.

The preparation method of the terahertz material with therapeutic and health care effect, comprising the following steps:

(1) mixing crude silicon, $SiO_2$ and Binchotan in a weight ratio of 1:3:5, and heating to 700° C. in an oxygen-free environment for 8 hours to obtain a black crystal $SiO_x$;

(2) mixing the prepared $SiO_x$ with other raw materials in accordance with the stated proportions, crushing, its fineness reaches 200~500 mesh, and adding an appropriate amount of water, stirring, being turn into a small ball through a circular rotary table, heating to 600° C. in an oxygen free environment for 8 hours, and carrying out a secondary crushing, its fineness reaches 3000~8000 mesh;

(3) detecting its infrared emissivity, which is ≥0.92, and then crushing and powdering process, its fineness reaches is more than 10000 mesh, after being enhanced by a plurality of terahertz irradiation line to obtain a terahertz material with therapeutic and health care effect, wherein the terahertz irradiation line for enhancing process is configured to have 1-7 different frequencies, which are $2.3 \times 10^{11}$, $5.5 \times 10^{11}$, $1.1 \times 10^{12}$, $2.3 \times 10^{12}$, $5.5 \times 10^{12}$, $1.1 \times 10^{13}$, $2.3 \times 10^{13}$ Hz respectively.

The structure of the terahertz irradiation source is the same as that in example 1.

Example 3

A terahertz material with therapeutic and health care effect, which includes the following raw materials in parts by weight: 28 $SiO_2$, 3 $Al_2O$, 3 selenium, 2 germanium, 15 $Fe_2O_3$, 35 ochre, 35 zinc oxide, 65 $CaCO_3$, 0.5 rare earth palladium, 1 $SiO_x$.

The preparation method of the terahertz material with therapeutic and health care effect, comprising the following steps:

(1) mixing crude silicon, $SiO_2$ and Binchotan in a weight ratio of 1:5:10, and heating to 1500° C. in an oxygen-free environment for 1 hour to obtain a black crystal $SiO_x$;

(2) mixing the prepared $SiO_x$ with other raw materials in accordance with the stated proportions, crushing, its fineness reaches 200~500 mesh, and adding an appropriate amount of water, stirring, being turn into a small ball through a circular rotary table, heating to 1200° C. in an oxygen free environment for 3 hours, and carrying out a secondary crushing, its fineness reaches 3000~8000 mesh;

(3) detecting its infrared emissivity, which is ≥0.92, and then crushing and powdering process, its fineness reaches is more than 10000 mesh, after being enhanced by a plurality of terahertz irradiation line to obtain a terahertz material with therapeutic and health care effect, wherein the terahertz irradiation line for enhancing process is configured to have 1-7 different frequencies, which are $2.3 \times 10^{11}$, $5.5 \times 10^{11}$, $1.1 \times 10^{12}$, $2.3 \times 10^{12}$, $5.5 \times 10^{12}$, $1.1 \times 10^{13}$, $2.3 \times 10^{13}$ Hz respectively.

The structure of the terahertz irradiation source is the same as that in example 1.

Exemplary Application 1

FIG. 1 shows a most basic application form of the present invention: using the physiotherapy tablet 4 made of the terahertz material for health care and treatment of the present invention and placing it on a lesion site 3, its anti-inflammatory and analgesic effect is faster than the plaster, and it can be reused.

The application of the terahertz material of the present invention in the physiotherapy tablet includes the following features:

1) The terahertz physiotherapy tablet can be placed in various pain parts of the body, and can be treated continuously for 24 hours. It can cure diseases quickly and the cured diseases are not easy to relapse.

2) It can treat sciatica, lumbar disc herniation, tenosynovitis, heel tendinitis, tennis elbow, various muscle and bone trauma and dysmenorrhea. It can quickly relieve stomach pain, insomnia, vertigo and atrial fibrillation.

3) The terahertz physiotherapy tablet has no nuclear radiation (particle radiation) and are safe for people. They are also safe in contact with people and will not be allergic.

4) When making the physiotherapy tablet, soft materials such as natural rubber and food grade silica gel can be used as the substrate and mixed with the terahertz material.

This scheme is very suitable for personal daily use.

Exemplary Application 2

Figure 2:
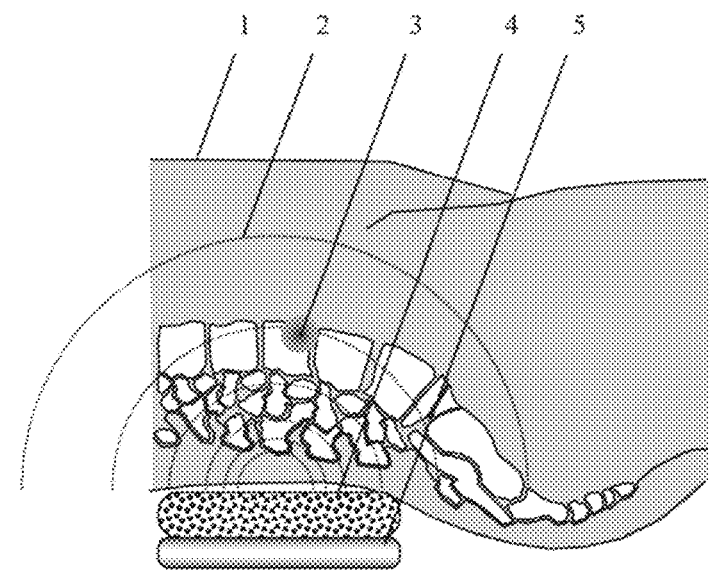
FIG. 2 shows a high temperature application of a physiotherapy tablet made of the above terahertz material with health treatment effect of the present invention.

A heater 5 is added to the scheme of the exemplary application 1 to expect the physiotherapy tablet 4 to emit a greater terahertz energy to reach deeper parts of the human body 1, or to treat a local discomfort faster, FIG. 2.

The application of the terahertz material of the present invention in the physiotherapy tablet includes the following features:

1) The heater can be various heating devices such as a warm baby, a warm water bag, a warm hand treasure, an electric heating sheet or an electric blanket. Users can choose according to their preferences and convenience.

2) The terahertz physiotherapy tablet can be placed in various pain parts of the body, and the continuous heating time is preferably no more than 2 hours. Compared with that of the exemplary application 1, it can cure the disease faster and the cured disease is not easy to relapse.

3) It is used for various diseases in the previous exemplary application, but cannot be used for insomnia, vertigo and atrial fibrillation.

4) The terahertz physiotherapy tablet has no nuclear radiation (particle radiation) and are safe for people. They are also safe in contact with people and will not be allergic.

5) When making the physiotherapy tablet, soft materials such as natural rubber and food grade silica gel can be used as the substrate and mixed with the terahertz material.

This scheme is also very suitable for personal daily use.

Exemplary Application 3

Figure 3:
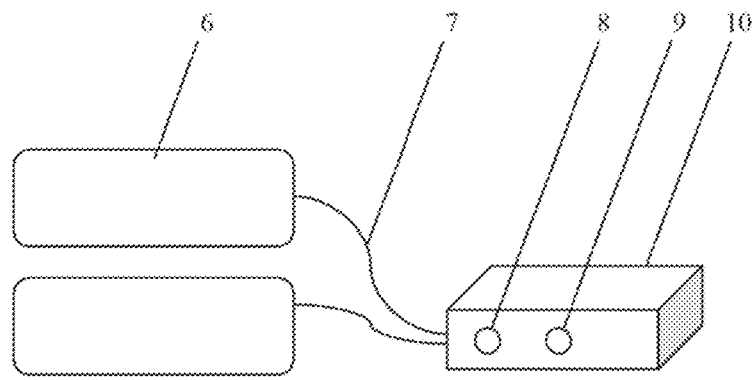
FIG. 3 shows a physiotherapy tablet and a physiotherapy instrument made of the above terahertz material with health treatment effect of the present invention.

FIG. 3 is a physiotherapy sheet 6 combining the terahertz physiotherapy tablet made of the terahertz material for health treatment with an electric heater, and cooperating a physiotherapy machine 10 equipped with a timing knob 8 and a temperature setting knob 9. The therapeutic effect and comfort are better than those in the exemplary application 2.

The application of the terahertz material of the present invention in the physiotherapy tablet includes the following features:

1) This device has an interesting way to use. Two physiotherapy tablets are placed on both sides of the human body or limbs, which has better and faster treatment effect.

2) The treatable diseases are basically the same as those in the exemplary application 2, the degree of convenience is not as good as that in embodiment 2, but the effect and comfort are significantly improved.

This scheme is suitable for families, hospitals, nursing homes, clubs and other occasions.

Exemplary Application 4

Figure 4:
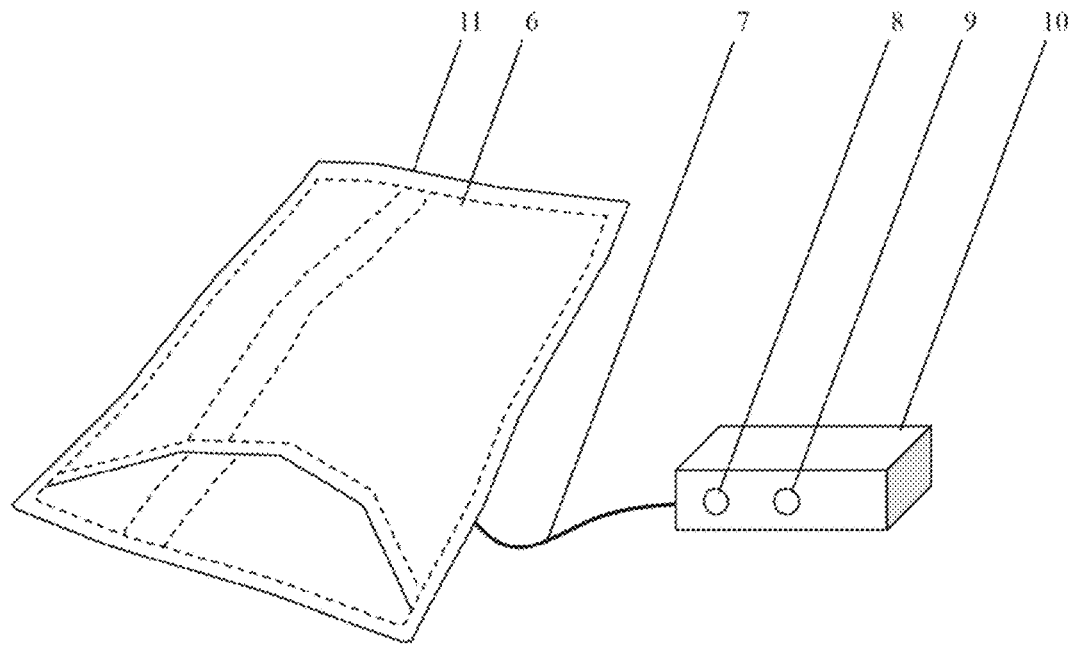
FIG. 4 shows a physiotherapy tablet and a physiotherapy sleeping bag made of the above terahertz material with health treatment effect of the present invention.

FIG. 4 shows a terahertz physiotherapy sleeping bag 11 defined from two physiotherapy sheets deformed and enlarged, and then connected to each other, which are shown in FIG. 3. In order to facilitate access to the sleeping bag, a hole should be provided in the side of the sleeping bag. The thermal insulation performance of the sleeping bag for physical therapy is not important for field survival. If users make a big blanket and users can cover the excess on your body after lying down, it can replace all the applications of the exemplary application 3.

The application of the terahertz material of the present invention in the physiotherapy tablet includes the following features:

1) This device can finally work on the whole body, and has a significant effect on recovering physical fitness for extremely weak and sick people.

2) The treatable diseases are basically the same as those in the exemplary application 2, and are also suitable for severe patients such as cancer.

2) its convenience is not as good as that in the exemplary application 2, but the effect and comfort are significantly improved.

4) The charging function can be added, and the charging organization or charging QR code can be used for business.

This scheme is suitable for families, nursing homes, clubs and other occasions.

Exemplary Application 5

Figure 5:
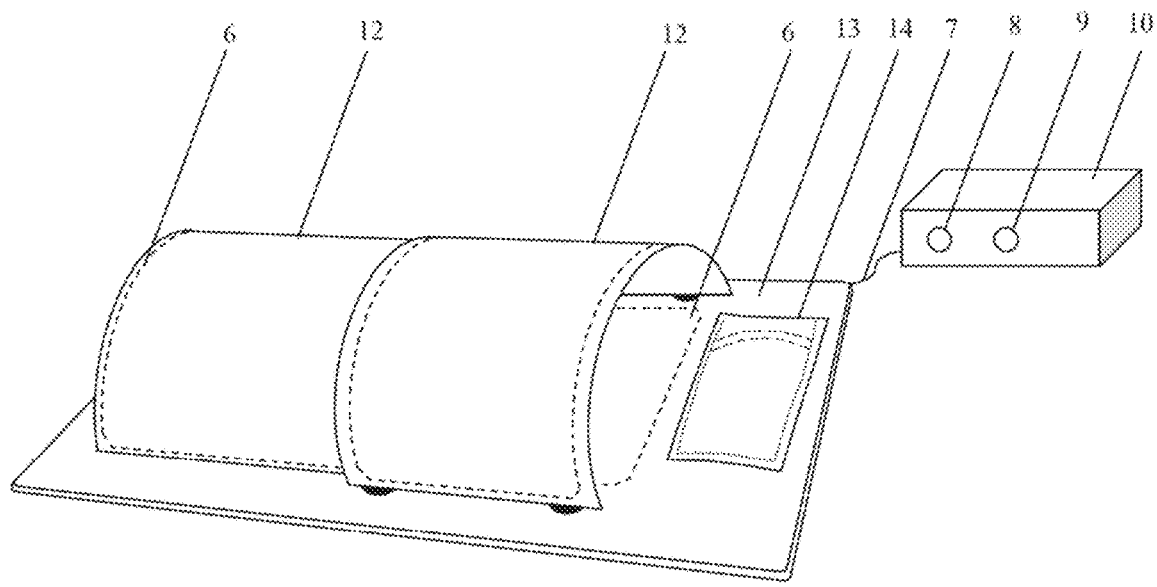
FIG. 5 shows a physiotherapy tablet and a tunnel physiotherapy warehouse made of the above terahertz material with health treatment effect of the present invention.

FIG. 5 shows a tunnel physiotherapy bedding defined from the physiotherapy sheets deformed, enlarged and hardened, which are shown in FIG. 4. The comfort of this equipment is significantly better than that of the exemplary application 4. In order to facilitate access, the tunnel is divided into multiple blocks (shown in FIG. 5). Electric, manual and other methods can be used to open and close the culvert. Different shell shapes do not affect the physiotherapy effect.

The application of the terahertz material of the present invention in the physiotherapy tablet includes the following features:

1) This device can work on the whole body, and has a significant effect on recovering physical fitness for extremely weak and sick people.

2) The treatable diseases are basically the same as those in the exemplary application 4.

4) its convenience is better that in the exemplary application 4, but the comfort are significantly improved.

3) The charging function can be added, and the charging organization or charging QR code can be used for business.

This scheme is suitable for (large space) families, hospitals, nursing homes, clubs and other occasions.

Exemplary Applications 6/7

Figure 6:
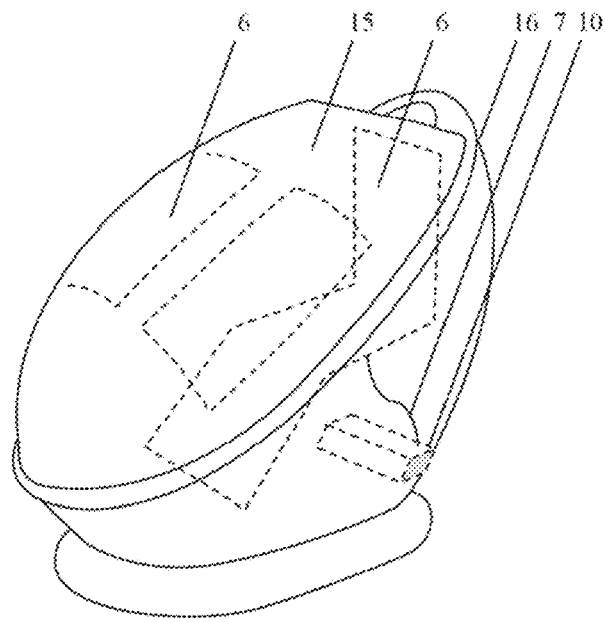
FIG. 6 shows a physiotherapy tablet and a sitting physiotherapy warehouse made of the above terahertz material with health treatment effect of the present invention.
Figure 9:
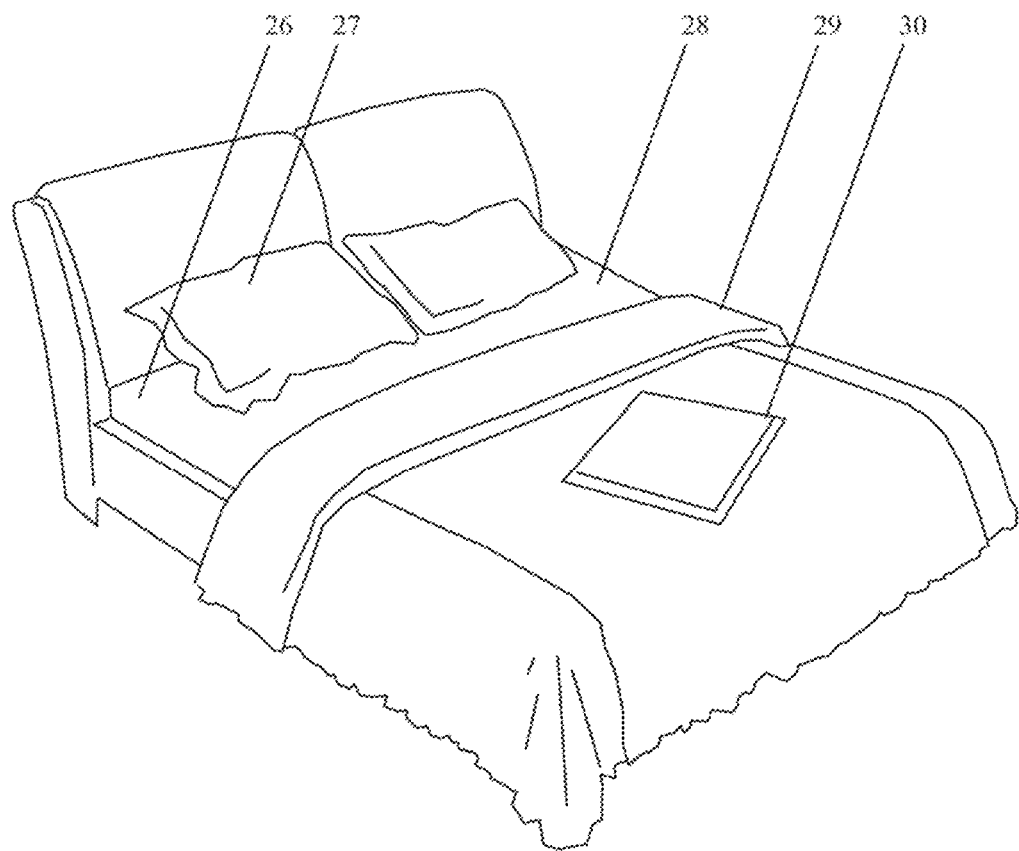
FIG. 9 shows a physiotherapy bedding made of the above terahertz material with health treatment effect of the present invention.

FIG. 6 and FIG. 7 show that the physiotherapy equipment of these two devices has the same therapeutic effect in sitting or lying mode. Each pf both devices has a body 16 and an upper cover 15. Both the upper cover and the body are provided with a combined physiotherapy sheet 6, which is connected to the physiotherapy instrument host 10 through a cable 7. Both devices have operation panels on which users can adjust the temperature and time by themselves.

The application of the terahertz material of the present invention in the physiotherapy tablet includes the following features:

1) This device can also be used for whole-body physiotherapy, which is the same as that of the exemplary applications 2 and 3, and has a significant effect on recovering physical fitness for extremely weak and sick people.

2) The treatable diseases are basically the same as those in the exemplary application 4.

4) its convenience is better that in the exemplary applications 4 and 5, but the comfort are significantly improved.

3) The charging function can be added, and the charging organization or charging QR code can be used for business.

This scheme is suitable for (large space) families, hospitals, nursing homes, clubs and other occasions.

Exemplary Applications 8/9

These two exemplary applications are various close fitting daily necessities produced by the combination of the terahertz material of the present invention, fabric, natural rubber and other materials. These physiotherapy equipments can be used in all forms from head to foot (except skirts).

The applications of the terahertz material of the present invention in the physiotherapy clothing and bedding include the following features:

1) physiotherapy hat 17 and its indications: dizziness, headache, insomnia (remove it during sleep and change physiotherapy pillow 27).

2) physiotherapy bra and bra pad and their indications: breast hyperplasia (hyperplasia still needs to be paid attention to after pain relief).

3) physiotherapy gloves and wristbands 19 and their indications: mouse hand, sprain (can be quickly cured).

4) physical therapy elbow protection 20 and its indications: mouse hand, sprain (can be quickly cured).

5) physiotherapy lumbar protection and its indications: thoracic pain and lumbar pain.

6) physiotherapy underwear 22 and its indications: long sitting buttock pain, tail vertebra pain, hemorrhoids, dysmenorrhea, prostatitis and impotence.

7) physiotherapy kneepad protection 23 and its indications: leg pain, arthritis.

8) physiotherapy ankle protection 24 and its indication: Sprain.

9) physiotherapy insole 25 and its indications: heel tendinitis, foot arch tendon strain, acupoint health care.

10) physiotherapy cushion 26 and its indications: open up blood and improve immunity.

11) physiotherapy pillow 27 and its indications: neurasthenia, insomnia, dizziness and tinnitus.

12) physiotherapy mattress 28 and its indications: open up blood and improve immunity.

13) physiotherapy quilt 29 and its indications: open up blood and improve immunity.

14) physiotherapy saddle 30 and its indications: long sitting buttock pain, tail vertebra pain, hemorrhoids, dysmenorrhea, prostatitis and impotence.

This scheme is suitable for families, nursing homes, clubs and other occasions.

Exemplary Applications 10/11

The dysmenorrhea treatment belt (shown in FIG. 14) and the dysmenorrhea treatment underwear (FIG. 15) used in this application are based on the current popular product forms of electric heating products for maintenance in physiological period, warm palace belt and underwear in physiological period plus warm baby, plus the terahertz physiotherapy tablet.

After many tests, it has been proved that the terahertz physiotherapy tablet can cure dysmenorrhea within 3~12 months. The physiotherapy tablet has fast action speed, stable effect and no side effects. These devices are reused and have a long service life.

Compared with the prior art, the dysmenorrhea treatment belt and the dysmenorrhea treatment underwear of the present invention have the following beneficial effects: 1) dysmenorrhea can be cured, but other means are not available; 2) During the treatment, the abdominal pain has been reduced a lot, which cannot be achieved by any other means; 3) After dysmenorrhea is cured, continue to use it in the physiological period, and the abdominal discomfort in the physiological period will be significantly reduced.

An application of the dysmenorrhea treatment belt with a terahertz physiotherapy tablet having a heating equipment of the present invention includes the following features:

1) The terahertz physiotherapy tablet and the heating sheet are stacked on the front of the belt, with internal integrated switch and temperature control circuit.

2) A power bank is placed on the side, which can heat continuously for several hours. Physiotherapy without heating is enough. After heating, the effect is better and more comfortable.

3) Bluetooth device can be built in to control the temperature and the heating switch by a mobile phone app.

4) The terahertz physiotherapy tablet has no nuclear radiation (particle radiation) and are safe for people. They are also safe in contact with people and will not be allergic.

The application of the physiological underwear and the warm baby combined with the terahertz physiotherapy tablet in the treatment of dysmenorrhea includes the following features:

1) The terahertz physiotherapy tablet and the heating sheet are stacked on the front of the belt.

2) The heating sheet can be used to warm the warm baby or electric heating sheet.

3) When using the warm baby, pay attention to the temperature and be careful of low temperature scald.

Treated Cases:

Case 1: Ms. Chen, 50 years old, has shoulder and neck pain and poor sleep quality. After a week of physical therapy in health terahertz physiotherapy bed, her sleep quality has been improved and she knows that she is sleepy. Her shoulder and neck are relaxed and comfortable.

Case 2: Mr. Hu, 60 years old, has cardiovascular and cerebrovascular disease, weak body and poor renal function. After two weeks of physical therapy in the health terahertz physiotherapy bed, his physical strength has recovered a lot. He can work for a long time. He is no longer as tired as usual, his cardiovascular disease has been controlled, he feels comfortable, his renal function has recovered well, his morning blooming function has been restored, and his male sexual function has been enhanced.

Case 3: Ms. Guo, 47, uterine cyst, breast hyperplasia, climacteric syndrome. After ten weeks of physical therapy in health terahertz physiotherapy bed, the chest feeling has improved significantly, the sleep quality has improved, the climacteric symptoms have been relieved, the mood is comfortable, and the gynecological problems have been controlled.

Case 4: Ms. Lu, 33, had severe menstrual pain and recovered three months after using physiotherapy tablets.

Case 5: Ms. He, 29, has menstrual pain. Sometimes it takes 2~3 days to come to her menstrual leave. Her blood is black. One year after the use of physiotherapy tablets, it was completely cured. Moreover, it was later found that even if there was no stomachache, it was more comfortable to use film during menstruation.

The basic principles and main features of the invention and the advantages of the invention are shown and described above. Those skilled in the art should understand that the invention is not limited by the above embodiments. What is described in the above embodiments and specifications is only to explain the principle of the invention. On the premise of not departing from the spirit and scope of the invention, the invention will have various changes and improvements, which fall within the scope of the claimed invention. The scope of protection claimed by the present invention is defined by the appended claims and their equivalents.

What is claimed is:

1. A composition for manufacturing a terahertz material, including the following raw materials in parts by weight: 15~28 $SiO_2$, 3~8 $Al_2O_3$, 1~3 selenium, 2~5 germanium, 10~15 $Fe_2O_3$, 35~45 ochre, 20~35 zinc oxide, 65~80 $CaCO_3$, 0.1~0.5 palladium, 1~10 $SiO_x$, wherein $SiO_x$ is made by mixing crude silicon, $SiO_2$ and Binchotan in a weight ratio of 1: (3~5): (5~10), and heating to 700~1500° C. in an oxygen-free environment for 1~8 hours to obtain a black crystal $SiO_x$.

2. The composition for manufacturing a terahertz material, as recited in claim 1, including the following raw materials in parts by weight: 20 $SiO_2$, 4 $Al_2O_3$, 2 selenium, 3 germanium, 12 $Fe_2O_3$, 40 ochre, 25 zinc oxide, 70 $CaCO_3$, 0.3 palladium, 5 $SiO_x$, wherein $SiO_x$ is made by mixing crude silicon, $SiO_2$ and Binchotan in a weight ratio of 1:4:8, and heating to 1200° C. in an oxygen-free environment for 3 hours to obtain a black crystal $SiO_x$.

3. The composition for manufacturing a terahertz material, as recited in claim 1, including the following raw materials in parts by weight: 15 $SiO_2$, 8 $Al_2O_3$, 1 selenium, 5 germanium, 10 $Fe_2O_3$, 45 ochre, 20 zinc oxide, 80 $CaCO_3$, 0.1 palladium, 10 $SiO_x$, wherein $SiO_x$ is made by mixing crude silicon, $SiO_2$ and Binchotan in a weight ratio of 1:3:5, and heating to 700° C. in an oxygen-free environment for 8 hours to obtain a black crystal $SiO_x$.

* * * * *